(12) United States Patent
Davis et al.

(10) Patent No.: US 8,852,944 B2
(45) Date of Patent: *Oct. 7, 2014

(54) QUANTUM DOT-BASED ENVIRONMENTAL INDICATORS

(75) Inventors: Keith J. Davis, Seattle, WA (US); Nicole L. DeHuff, Seattle, WA (US); Morteza Safai, Seattle, WA (US)

(73) Assignee: The Boeing Company, Chicago, IL (US)

( * ) Notice: Subject to any disclaimer, the term of this patent is extended or adjusted under 35 U.S.C. 154(b) by 208 days.

This patent is subject to a terminal disclaimer.

(21) Appl. No.: 13/070,046

(22) Filed: Mar. 23, 2011

(65) Prior Publication Data

US 2011/0176962 A1 Jul. 21, 2011

Related U.S. Application Data

(63) Continuation of application No. 12/335,724, filed on Dec. 16, 2008, now Pat. No. 7,955,858.

(51) Int. Cl.
| | |
|---|---|
| *G01N 21/75* | (2006.01) |
| *G01N 21/76* | (2006.01) |
| *B82Y 5/00* | (2011.01) |
| *G01N 21/64* | (2006.01) |
| *G01N 33/32* | (2006.01) |
| *G01N 17/04* | (2006.01) |
| *B82Y 15/00* | (2011.01) |
| *B82Y 20/00* | (2011.01) |
| *C09D 5/33* | (2006.01) |
| *C09D 7/12* | (2006.01) |

(52) U.S. Cl.
CPC ............... *G01N 21/64* (2013.01); *G01N 33/32* (2013.01); *G01N 17/04* (2013.01); *B82Y 15/00* (2013.01); *B82Y 20/00* (2013.01); *C09D 5/004* (2013.01); *C09D 7/1291* (2013.01)
USPC ................................. 436/2; 436/73

(58) Field of Classification Search
USPC .......... 436/2, 5, 6, 37, 73, 164, 172; 422/400; 252/301.36, 301.4 R, 301.5, 301.6 R, 252/301.6 S, 301.6 P, 301.6 F, 301.4 S, 252/301.4 P, 301.4 F, 301.4 H, 408.1, 600
See application file for complete search history.

(56) References Cited

U.S. PATENT DOCUMENTS

| | | | |
|---|---|---|---|
| 5,411,890 | A | 5/1995 | Falat |
| 6,564,620 | B1 | 5/2003 | Jaeger |
| 6,710,366 | B1 | 3/2004 | Lee et al. |
| 7,304,305 | B2 | 12/2007 | Hunt |

(Continued)

FOREIGN PATENT DOCUMENTS

WO 2006107493 A1 10/2006

OTHER PUBLICATIONS

"Group (periodic table)." Wikipedia entry. Accessed by the examiner on Feb. 8, 2012, accessed at <http://en.wikipedia.com/wiki/Group (periodic table)>.*

(Continued)

*Primary Examiner* — Christopher A Hixson
(74) *Attorney, Agent, or Firm* — Smith Moore Leatherwood LLP

(57) ABSTRACT

A detection method and indicator are disclosed that includes quantum dots that fluoresce under illumination of a first light having a first wavelength to indicate the presence of a predetermined condition, and in particular, a corrosion condition. The quantum dots are surrounded by a shell material that under normal conditions reflect the first light and reacts in the presence of the predetermined condition to permit the first light to illuminate the quantum dot to excite the quantum dot to emit a second light having a second wavelength, which when detected, indicates the presence of the predetermined condition.

14 Claims, 3 Drawing Sheets

(56) References Cited

U.S. PATENT DOCUMENTS

| | | | |
|---|---|---|---|
| 2003/0068824 A1 | 4/2003 | Frankel et al. | |
| 2005/0200481 A1* | 9/2005 | Wallach | 340/541 |
| 2006/0062902 A1 | 3/2006 | Sager et al. | |
| 2006/0068203 A1* | 3/2006 | Ying et al. | 428/403 |
| 2007/0042139 A1 | 2/2007 | Cooper et al. | |
| 2007/0048867 A1 | 3/2007 | Farmer | |
| 2007/0110960 A1 | 5/2007 | Frey et al. | |
| 2007/0264719 A1 | 11/2007 | Santra et al. | |
| 2008/0057304 A1 | 3/2008 | Fristad et al. | |
| 2008/0241071 A1* | 10/2008 | West et al. | 424/9.6 |

OTHER PUBLICATIONS

Yu, W. William et al. "Experimental determination of the extinction coefficient of CdTe, CdSe, and CdS nanocrystals." Chem. Mater. (2003) 15 2854-2860.*

UCI Website. "Advantages of quantum dots over conventional fluorophores." Found on the web at <http://bme240.eng.uci.edu/students/07s/yokabe/advantages.htm>.*

Saito, Masaaki et al. "Development aluminum bodies for fuel efficient vehicles." Materials Today (2001) 4 30-34.*

Artemyev, M.V. et al., "Quantum dots in photonic dots", Applied Physics Letter (2006) 76, p. 1353-1355.

Bryant, D.E. et al., "The use of fluorescent probes for the detection of under-film corrosion", Progress in Organic Coatings, (2006), 57, pp. 416-420.

Hakim, Luis F. et al., "Nanocoating individual silica nanoparticles by atomic layer deposition in a fluidized bed reactor", Chemical Vapor Deposition, (2005), 11, pp. 420-425.

http://www.sciencelab.com/page/S/PVAR/SLA3115, Science Lab. com Chemicals & Laboratory Equipment, pp. 1-2, dated Oct. 23, 2009.

* cited by examiner

QUANTUM DOT-BASED ENVIRONMENTAL INDICATORS

FIELD OF DISCLOSURE

This invention relates generally to a method, system, indicator and coating for the non-destructive detection of a predetermined condition. The invention relates more specifically to a method, system, indicator and coating that uses quantum dots that fluoresce under illumination to indicate the presence of a predetermined condition, and in particular, a corrosion condition.

BACKGROUND

The early detection of corrosion on metallic structures and vehicles is an extremely time-consuming, costly and difficult task that implicates significant economic and safety considerations. For example, aircraft, spacecraft, automotive vehicles, watercraft, and various military vehicles operate and/or are exposed to corrosive environments.

For example, military and commercial aircraft undergo routine pre-flight, post-flight and periodic corrosion inspections and corrective maintenance. Often very expensive and time consuming techniques, such as x-ray radiography, ultrasonic imaging, and electromagnetic eddy current inspection methods may be used to detect corrosion. For many applications, damage due to corrosion is often difficult to detect. This is especially problematic on surfaces that are difficult to access with detection equipment.

In the past, various approaches have been employed and sensors developed to detect corrosion of metallic structures including the use of coatings applied to structure surfaces to sense corrosion. One approach that has been attempted to apply coatings intended to act as a sensor reactive to corrosion. For example, color-change pH indicators have been incorporated into organic coatings for determining the pH gradients associated with corrosion. In another example, fluorescent dyes have been applied to microelectronic test vehicles to detect pH changes associated with corrosion of aluminum or gold metallization under an applied electrical bias in a humid environment. Other attempts have included the use of fluorescing and color-change dyes that have been applied to aluminum after corrosion has begun in order to identify the location of the hydrous aluminum oxide corrosion product. More recently, paint has been formulated to include different chemicals that fluoresce upon oxidation or upon complex-action with metal cations formed by the corrosion process.

Many prior fluorescent and luminescent paints have required that a large portion of the coating be a visual indicator. Such a large concentration of the additive may negatively affect the performance of the coating. Moreover, many types of pigments alter the coating color and appearance. Such indicators are typically organic based compositions that may deteriorate and lose their usefulness over time. The organic indicators may also migrate between coats, so it may not be apparent after time has passed whether a second layer was satisfactorily applied. In addition, many indicators do not show fluorescence in a color that is easy for the human eye to detect, so that the contrast between the coating and the uncoated areas are not readily detected.

However, no method, system or coating has been developed that provides an inexpensive and more comprehensive technique for visually revealing locations of corrosion, even in difficult to inspect locations.

Therefore, a system, method and coating is needed for improved corrosion detection. Such a system, method and coating should provide for simple, effective application, reliable overall coating, and simple corrosion detection.

The foregoing examples and limitations associated therewith are intended to be illustrative and not exclusive. Other limitations of the related art will become apparent to those of skill in the art upon reading of the specifications and study of the drawings.

SUMMARY

The following embodiments and aspects thereof are described and illustrated in conjunction with systems and methods that are meant to be exemplary and illustrative, not limiting in scope. In various embodiments, one or more of the problems described above in the Background have been reduced or eliminated, while other embodiments are directed to other improvements.

According to one exemplary embodiment, a detection method is disclosed that includes applying a coating to a substrate, illuminating the applied coating with a first light having a first predetermined wavelength and detecting a second light having a second predetermined wavelength. The coating includes a microsphere comprising a quantum dot and a shell surrounding the quantum dot, and the shell is formed of a shell material that reflects the first light. The quantum dot is selected to emit the second light when illuminated by the first light. The shell material selected to react in the presence of a predetermined condition to allow the first light to illuminate the quantum dot.

According to another exemplary embodiment, an indicator is disclosed that includes a quantum dot configured to emit a second light having a second wavelength when illuminated by a first light having a first wavelength, and a shell surrounding the quantum dot. The shell is formed of a material that reflects the first light and reacts in the presence of a predetermined condition to allow the first light to illuminate the quantum dot.

According to another exemplary embodiment, a sensing system is disclosed that includes a substrate, a coating disposed upon the substrate, a light illumination source providing a first light having a first wavelength directed at the substrate, and a light detection device for detecting a second light having a second wavelength. The coating comprises a microsphere comprising a quantum dot and a shell surrounding the quantum dot. The quantum dot is selected to emit the second light when illuminated by the first light. The shell is formed of a shell material that reflects the first light and reacts in the presence of a predetermined condition to allow the first light to illuminate the quantum dot.

According to yet another exemplary embodiment, an article is disclosed that includes a substrate and a coating upon the substrate, the coating including a microsphere having a quantum dot and a shell surrounding the quantum dot. The quantum dot is selected to emit a second light having a second predetermined wavelength when illuminated by a first light having a first predetermined wavelength. The shell is formed of a shell material that reflects the first light and reacts in the presence of a predetermined condition to allow the first light to illuminate the quantum dot.

One advantage of the present disclosure includes a method, system and coating for detecting an environmental condition by emission of specific wavelengths of light.

Another advantage of the present disclosure includes a method, system and coating for detecting a corrosive condition by emission of specific wavelengths of light.

Another advantage of the present disclosure includes a method, system and coating for indicating corrosion of a substrate by emission of specific wavelengths of light.

Another advantage of the present disclosure includes a method, system and coating that provides for objective, quantitative evidence of corrosive conditions allowing for an indication of corrosion at an early stage, and in particular, before significant corrosion of the substrate.

Another advantage of the present disclosure includes a method, system and coating that permits a high degree of automation in the corrosion inspection process and related documentation.

Further aspects of the method and apparatus are disclosed herein. Other features and advantages of the present disclosure will be apparent from the following more detailed description of the preferred embodiment, taken in conjunction with the accompanying drawings that illustrate, by way of example, the principles of the disclosed embodiment of the disclosure. The features, functions, and advantages of the present disclosure can be achieved independently in various embodiments of the present disclosure or may be combined in yet other embodiments.

BRIEF DESCRIPTION OF THE DRAWINGS

Wherever possible, the same reference numbers will be used throughout the drawings to refer to the same or like parts.

DETAILED DESCRIPTION

The embodiments disclosed will now be described more fully hereinafter with reference to the accompanying drawings, in which preferred embodiments of the disclosure are shown. However, one must note that various functions and features may be embodied in many different forms and should not be construed as limited to the embodiments set forth herein; rather, these embodiments are provided so that this disclosure will be thorough and complete and will fully convey the scope of the invention to those skilled in the art. All composition percents are given as weight percents, unless otherwise specified.

According to disclosed embodiments, the present disclosure includes a visual corrosion indictor including a method, system and coating for non-destructive visual indication of corrosion for use in environments that are either corrosive in nature and/or potentially corrosive. The visual corrosion indicator may be used to indicate the presence of a corrosive condition and/or corrosion of a substrate. The visual corrosion indicator produces a visual display indicative of the presence of a corrosive environment or corrosion.

Figure 1:
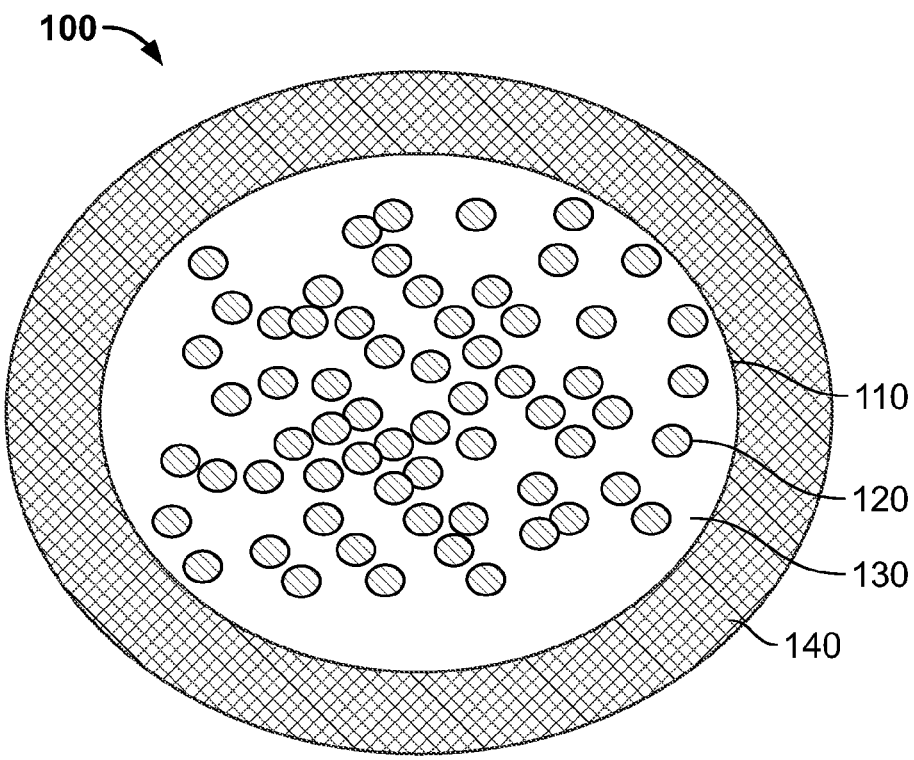
FIG. 1 shows an exemplary microsphere of the present disclosure.

FIG. 1 shows an exemplary microsphere 100 according to the disclosure. As can be seen in FIG. 1, microsphere 100 includes a core 110 including a plurality of quantum dots (QDs) 120 in an optically clear host matrix 130. The core 110 is surrounded by a shell 140. The microsphere 100 has a generally spherical geometry having a diameter ranging from about 1 µm to about 5 µm. In another exemplary embodiment, the microsphere 100 may have at least one QD 120. In another embodiment, the microsphere 100 may have other geometries, including but not limited to ellipsoidal, cubic, oval or other shape.

The QDs 120 are nanoparticles formed of a semiconductor material having a maximum geometric length of between about 1 nm and 50 nm. In another embodiment, the maximum geometric length may be between about 2 nm and 10 nm. In yet another embodiment, the maximum geometric length may be about 4 nm. The QDs 120 have "artificial" band gaps that are wider for smaller particles. The QDs 120 absorb light over a broad spectrum, but emit light over a narrow band of wavelengths with photon energies close to that of the bandgap. QDs have been previously discussed, for example, in U.S. Pat. No. 6,710,366, issued Mar. 23, 2004, which is incorporated herein by reference in it's entirety.

The core 110 exposed to light at wavelengths shorter than the emission wavelength of the QDs 120 will emit light in a narrow wave band characteristic of the imbedded QDs 120.

The matrix 130 is formed of transparent or translucent material. In one embodiment, the matrix 130 may be a polymer, resin, sol get, or other organic or inorganic material.

The shell 140 coats the core 110 and is selected to reflect a first light, such as an illumination or interrogation light of a predetermined frequency, so that no QD-emitted light can be measured. The shell 140 is also selected to react in the presence of a predetermined condition to allow the first light to illuminate the quantum dot 120.

In one embodiment, the thickness of the shell 140 is selected to react with the predetermined condition at a predetermined rate. In another embodiment, the shell material forming the shell 140 is selected to react with the predetermined condition at a predetermined rate.

In one embodiment, the shell 140 is formed of an organic or inorganic reflective material. In another embodiment, the shell 140 is formed of an inorganic material. For example, the shell 140 may be formed of a metal or metal alloy. In one embodiment, the shell 140 is formed of aluminum. In another embodiment, the shell 140 is formed of an aluminum alloy. In yet another embodiment, the shell 140 is formed of a metal or metal alloy selected to corrode at a predetermined rate under predetermined environmental conditions. In yet another embodiment, the shell 140 is formed of the same material as the substrate.

In the presence of a corrosive condition or environment, the shell 140 can be corroded or otherwise become sufficiently transparent to light illuminating the microsphere 100. In one embodiment, the shell 140 may be formed of a material that converts or otherwise forms a non-metallic compound that is sufficiently transparent at some predetermined amount of corrosion for light to penetrate to the core 110 and for the QDs to emit light that escapes the microsphere 100. In another embodiment, the shell 140 may dissolve, disintegrate or otherwise degrade to become sufficiently transparent to light illuminating the microsphere 100. The emitted light may be detected by a spectrally filtered imaging device or system as an indication of corrosion. In one embodiment, the amount of corrosion is recorded to form a record of the progression of the detected corrosion.

Figure 2:
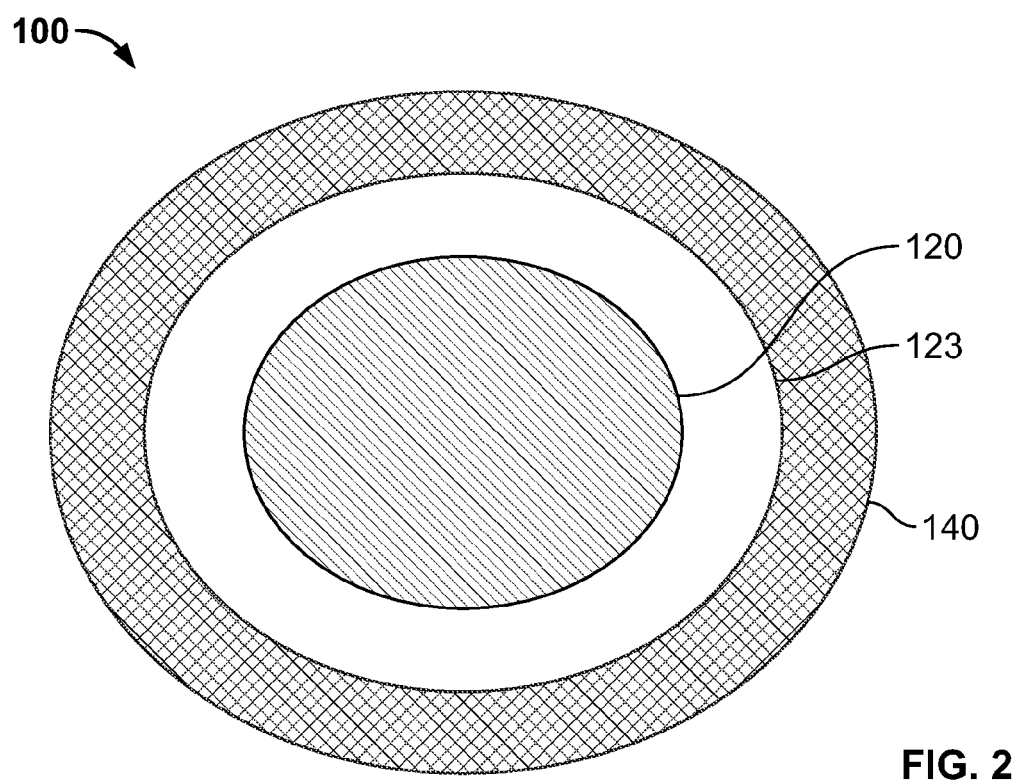
FIG. 2 shows another exemplary microsphere of the present disclosure.

FIG. 2 shows another embodiment of microsphere 100. In this embodiment, microsphere 100 includes a QD 120 surrounded by an inner shell 123, which is in turn surrounded by shell 140. In another embodiment, the shell 123 may surround one or more QDs 120. For example, the shell 123 may surround a plurality of QDs in a matrix 130. The inner shell 123 is depicted as a single shell layer, however, in another embodiment, the inner shell 123 may be formed of one or more shell layers. The inner shell 123 may be formed of an inorganic or organic material. In another embodiment, the inner shell 123 may be formed of formed of a material that converts or otherwise forms a non-metallic compound that is sufficiently transparent at some predetermined amount of corrosion for light to penetrate to the core 110 and for the QDs to emit light that escapes the microsphere 100. In another embodiment, the inner shell 123 may be formed of an inorganic material. For example, the inner shell 123 may be formed of a metal or metal alloy. In one embodiment, the inner shell 123 is formed of aluminum. In another embodiment, the inner shell 123 is formed of an aluminum alloy. In yet another embodiment, the inner shell 123 is formed of a metal or metal alloy selected to corrode at a predetermined rate under predetermined environmental conditions.

Figure 3:
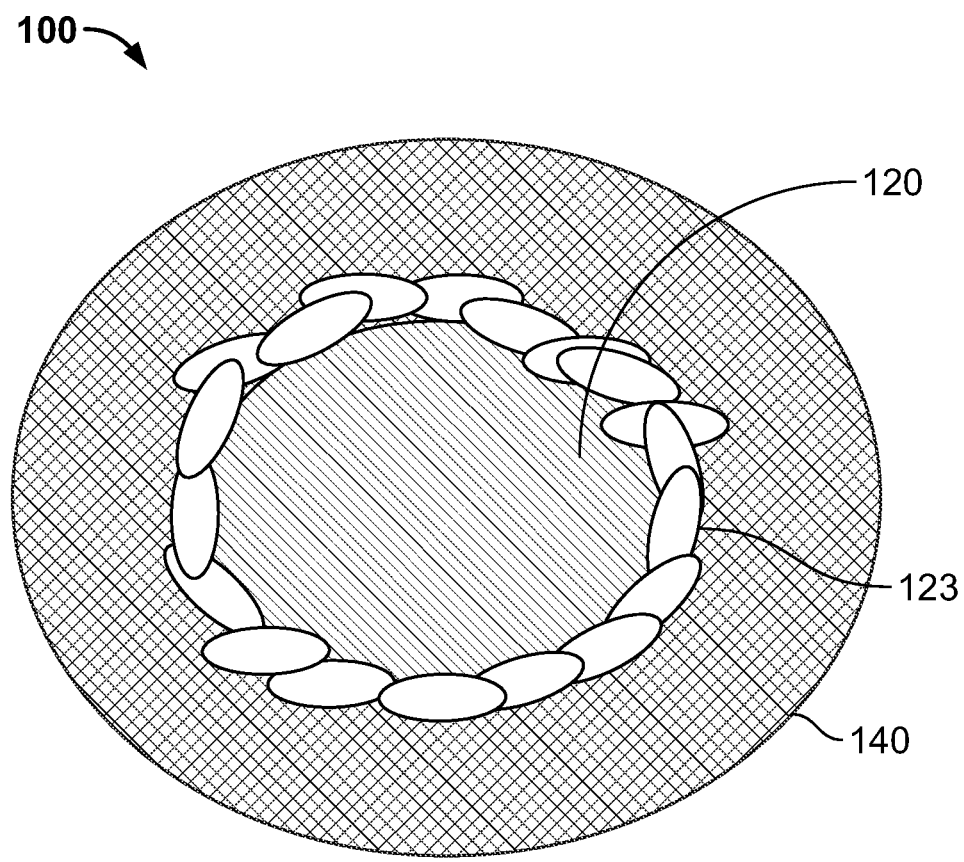
FIG. 3 shows another exemplary microsphere of the present disclosure.

FIG. 3 shows yet another embodiment of microsphere 100. In this exemplary embodiment, microsphere 100 includes a single QD 120 surrounded by an inner coating 123, which is in turn surrounded by shell 140. The inner coating 123 may be formed of a long-chain molecule. In one example, the inner coating 123 may be formed of polymer. In yet another embodiment, the inner coating 123 is formed of a long chain molecule selected to corrode, oxidize or otherwise degrade at a predetermined rate under predetermined environmental conditions.

Figure 4:
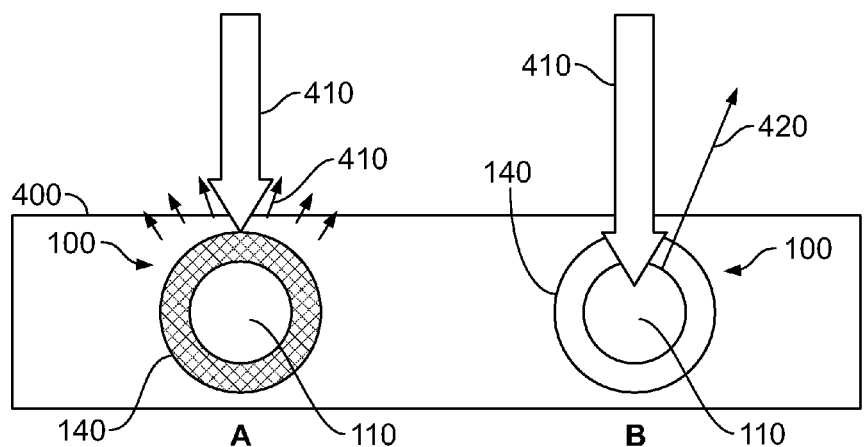
FIG. 4 is an illustration of an exemplary application of the disclosure.

FIG. 4 shows a microsphere 100 in a non-corroded state "A" and in a corroded state "B" in a coating layer 400. As can be seen in FIG. 4, a microsphere 100 having a core 110 and a shell 140 in non-corroded state "A", when interrogated or illuminated by a first light 410 having a preselected wavelength, reflects the first light 410. In one embodiment, the first light 410 has a first wavelength in the range of about 100 nm to about 3000 nm. In another embodiment, the first light 410 has a first wavelength in the range of about 300 nm to about 2000 nm. In yet another embodiment, the first light 410 has a first wavelength in the range of about 300 nm to about 1000 nm. The first light wavelength may be a broad range or very narrow range. For example, a broad range may be from a first light source such as the sun. In another example, a narrow range may be from a first light source such as a laser. As further shown in FIG. 4, a microsphere 100 having a shell 140 in corroded state "B", when illuminated by a first light 410, emits a second light 420 having a second wavelength, which can be detected and interpreted as evidence of shell degradation. In one embodiment, the detection of the second light may be an indication of an environmental condition corrosive to a substrate. In one embodiment, the second light 420 may have a wavelength in the range of about 300 nm to about 5000 nm as determined by the quantum dot properties and environment. In another embodiment, the second light 420 may have a wavelength in the range of about 300 nm to about 3000 nm as determined by the quantum dot properties and environment. In one embodiment, the coating layer 400 may be a paint, a primer, a sealant, a protective coating or other layer that provides for the quantum dot layer.

In one embodiment, the first light 410 may be provided from a light source, including but not limited to sunlight, incandescent light source, photodiode, laser or other suitable source of light. In one embodiment, the second light 420 may be detected by a detection system such as, but not limited to a visual detection by an operator, photodiode, or other imaging or non-imaging light detecting instrument. In one embodiment, the detection system may additionally include a spectral filter or other wavelength selective component.

In one exemplary embodiment, microspheres are fabricated that include QDs selected to emit red light when illuminated by blue light. In this embodiment, the microspheres are exposed to a blue light from an intense light emitting diode (LED) source, and the emitted light is detected by an operator using a spectrally filtered imaging device. In one embodiment, the spectrally filtered imaging device is filtered glasses that block most of the light at the illumination wavelength (blue light) but pass red wavelengths emitted by the QDs. The operator would be able to identify if microspheres have been corroded, since they would be observed emitting red light. In another embodiment, the operator uses a detector tuned to indicate the presence of a predetermined wavelength of light.

Figure 5:
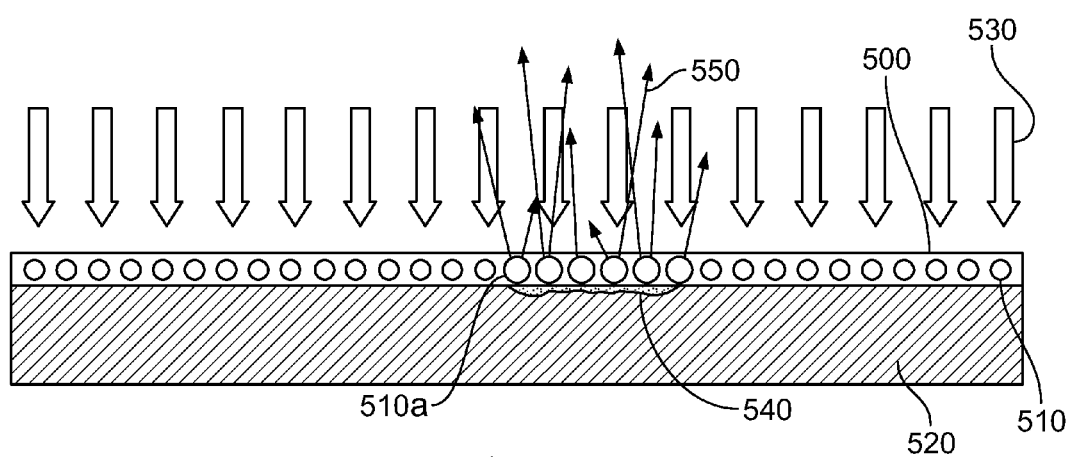
FIG. 5 shows an illustration of an exemplary application of the present disclosure.

FIG. 5 shows an exemplary application of a coating layer 500 including microspheres 510 upon a substrate 520. The microspheres 510 may be of any embodiment of microsphere as discussed above. As shown in FIG. 5, the coating layer 500 is illuminated with a first light 530. The first light 530 penetrates the coating layer 500 and illuminates the microspheres 510. The substrate 520 and coating layer 500 include a corrosion region 540. The microspheres 510a proximate the corrosion region emit an emission 550 in response to illumination by the first light 530. An operator can detect the emission and determine the extent of the corrosion region 540. In one embodiment, the substrate 520 may be an aluminum skin, for example, of an aircraft structure. In another embodiment, the corrosion region 540 has not extended to the substrate 520, and only the microspheres 510 in a corrosive region of the coating layer 500 are corroded, not the substrate 520.

While this disclosure has discussed in the context of corrosion detection, QD loaded microspheres may be tailored to indicate other chemical processes by the selection of the shell material. For example, the dissolution of a microsphere shell may serve as an indicator of acidity, temperature, humidity, air or water pollution or other environmental conditions.

While exemplary embodiments of the disclosure have been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. It is therefore further intended that the following appended claims and claims hereafter introduced are interpreted to include all such modifications, permutations, additions, and sub-combinations as are within their true spirit and scope.

The invention claimed is:
1. An article comprising:
a substrate; and
a coating overlying the substrate,
the coating comprising: at least one microsphere having a core including one or more quantum dots formed from a semiconductor material and a shell surrounding the core,
wherein the one or more quantum dots emit a second light having a second wavelength when illuminated by a first light having a first wavelength;
wherein the shell comprises a material that reflects the first light; and
wherein the shell is formed of a material selected to degrade in the presence of an environmental condition corrosive to the substrate such that the shell becomes sufficiently transparent to allow the first light to penetrate the shell and illuminate the one or more quantum dots.

2. The article of claim 1, wherein the at least one microsphere further comprises an inner shell disposed between the shell and the core of the microsphere.

3. The article of claim 1, wherein the quantum dots are disposed in a polymer matrix.

4. The article of claim 1, wherein the coating further comprises at least one material selected from the group consisting of a paint, a sealant, and a primer.

5. The article of claim 1, wherein the shell of the microsphere is formed of a metal or metal alloy.

6. The article of claim 1, wherein the first wavelength is between about 100 nm and about 3000 nm and the second wavelength is between about 300 nm and about 5000 nm.

7. The article of claim 1, wherein the one or more quantum dots within the core have a maximum geometric length between about 1 nm and about 50 nm.

8. The article of claim 7, wherein the one or more quantum dots have a maximum geometric length between about 2 nm and about 10 nm.

9. The article of claim 1, wherein the one or more quantum dots have a maximum geometric length of about 4 nm.

10. The article of claim 1, wherein, in the presence of an environmental condition corrosive to the substrate, the quantum dots absorb an incident light and emit an emitted light, the emitted light including no measurable light having the wavelength of the incident light.

11. The article of claim 1, wherein the microsphere has a spherical geometry having a diameter between about 1 μm and about 5 μm.

12. The article of claim 1, wherein the shell is selected to degrade at a predetermined rate under predetermined environmental conditions.

13. The article of claim 1, wherein the shell is formed of the same material as the substrate.

14. The article of claim 5, wherein the shell of the microsphere is formed of a metal or metal alloy selected from the group consisting of aluminum and alloys of aluminum.

* * * * *